US010905695B2

(12) United States Patent
Lee et al.

(10) Patent No.: US 10,905,695 B2
(45) Date of Patent: Feb. 2, 2021

(54) OPHTHALMIC COMPOSITION FOR LOWERING INTRAOCULAR PRESSURE

(71) Applicant: TAEJOON PHARMACEUTICAL CO., LTD., Seoul (KR)

(72) Inventors: Joon Youb Lee, Seoul (KR); Youn Jae Shin, Gyeonggi-do (KR); Min Ji Lee, Gyeonggi-do (KR)

(73) Assignee: TAEJOON PHARMACEUTICAL CO., LTD., Seoul (KR)

( * ) Notice: Subject to any disclaimer, the term of this patent is extended or adjusted under 35 U.S.C. 154(b) by 0 days.

(21) Appl. No.: 16/347,901

(22) PCT Filed: Jun. 28, 2017

(86) PCT No.: PCT/KR2017/006857
§ 371 (c)(1),
(2) Date: May 7, 2019

(87) PCT Pub. No.: WO2018/088663
PCT Pub. Date: May 17, 2018

(65) Prior Publication Data
US 2019/0307768 A1 Oct. 10, 2019

(30) Foreign Application Priority Data

Nov. 9, 2016 (KR) .................. 10-2016-0148858
Jan. 6, 2017 (KR) .................. 10-2017-0002444

(51) Int. Cl.
*A61K 31/5575* (2006.01)
*A61K 9/08* (2006.01)
*A61K 47/26* (2006.01)
*A61K 47/44* (2017.01)
*A61P 27/02* (2006.01)
*A61P 27/06* (2006.01)
*A61K 9/00* (2006.01)

(52) U.S. Cl.
CPC ........ *A61K 31/5575* (2013.01); *A61K 9/0048* (2013.01); *A61K 47/26* (2013.01); *A61K 47/44* (2013.01); *A61P 27/02* (2018.01)

(58) Field of Classification Search
CPC .. A61K 31/5575; A61K 9/0048; A61K 47/26; A61K 47/44
See application file for complete search history.

(56) References Cited

U.S. PATENT DOCUMENTS

| 8,772,337 | B2 | 7/2014 | Pilotaz et al. | |
|---|---|---|---|---|
| 2009/0169629 | A1* | 7/2009 | Lambert | A61K 9/0048 424/489 |
| 2010/0210720 | A1 | 8/2010 | Pilotaz et al. | |
| 2010/0216877 | A1 | 8/2010 | Kshirsagar et al. | |
| 2011/0065790 | A1 | 3/2011 | Yoda et al. | |
| 2011/0319487 | A1* | 12/2011 | Mercier | A61K 9/0048 514/530 |
| 2012/0232139 | A1 | 9/2012 | Ueno et al. | |

FOREIGN PATENT DOCUMENTS

| JP | 5657789 B2 | 1/2015 |
|---|---|---|
| KR | 10-2001-0041473 A | 5/2001 |
| KR | 10-2011-0011707 A | 2/2011 |
| KR | 10-2013-0112728 A | 10/2013 |
| KR | 10-1529093 B1 | 6/2015 |
| RU | 2460516 C2 | 9/2012 |
| RU | 2482851 C2 | 5/2013 |
| WO | WO-99/51273 A1 | 10/1999 |
| WO | WO-2008/128779 A1 | 10/2008 |
| WO | WO-2009/145356 A1 | 12/2009 |
| WO | WO-2012/001009 A1 | 1/2012 |

OTHER PUBLICATIONS

Kim, S. J., et al.; "Effect of Preservative-free Artificial Eye Drop on Human Corneal Epithelial Cell in vitro", J Korean Ophthalmol Soc, 2010; 51(8), pp. 1113-1120.
Smedowski, A., et al.; "Excipients of preservative-free latanoprost induced inflammatory response and cytotoxicity in immortalized human HCE-2 corneal epithelial cells", Journal of Biochemical and Pharmacological Research, vol. 2 (4): 175-184, Dec. 2014.
Rodriguez-Aller, M., et al.; "New prostaglandin analog formulation for glaucoma treatment containing cyclodextrins for improved stability, solubility and ocular tolerance", European Journal of Pharmaceutics and Biopharmaceutics, 2015, pp. 203-214.
Public Assessment Report, Scientific Discussion, MONOPROST 50 Micrograms/ml Eye Drops Solution in Single-dose Container (latanoprost), FR/H/0499/001/Dc, inner pp. 1-7, Sep. 15, 2016.
Office Action from corresponding Korean Patent Application No. 10-2017-0002444, dispatched on Jan. 25, 2017.
International Search Report from corresponding PCT Application No. PCT/KR2017/006857, dated Oct. 24, 2017.
Extended European Search Report from corresponding European Patent Application No. 17869084.8, dated May 26, 2020.
Office Action from corresponding Russian Patent Application No. 2019117769, dated Sep. 15, 2020.
Search Report from corresponding Russian Patent Application No. 2019117769, dated Sep. 15, 2020.
Office Action from corresponding Korean Patent Application No. 10-2017-0147784, dated Sep. 29, 2020.

* cited by examiner

*Primary Examiner* — Irina Neagu
(74) *Attorney, Agent, or Firm* — Harness, Dickey & Pierce, P.L.C.

(57) ABSTRACT

The present invention relates to an ophthalmic composition for lowering an intraocular pressure, the composition comprising latanoprost, polyoxyl 40 hydrogenated castor oil, and sorbitol.

17 Claims, 6 Drawing Sheets

OPHTHALMIC COMPOSITION FOR LOWERING INTRAOCULAR PRESSURE

CROSS-REFERENCE TO RELATED APPLICATIONS

This application is a national phase application of PCT Application No. PCT/KR2017/006857, filed on 28 Jun. 2017, which claims the benefit and priority to Korean Patent Application Nos. 10-2016-0148858, filed on 9 Nov. 2016 and 10-2017-0002444, filed on 6 Jan. 2017. The entire disclosures of the applications identified in this paragraph are incorporated herein by references.

FIELD

The present invention relates to an ophthalmic composition comprising latanoprost, polyoxyl 40 hydrogenated castor oil and sorbitol.

BACKGROUND

Glaucoma is one of the leading causes of blindness worldwide along with cataract and diabetic retinopathy, and the prevalence is about 2% of a population groups, such that glaucoma is considered as one of the most common ophthalmologic diseases. The glaucoma is characterized by having damage to optic nerves accompanied by a loss of retinal ganglion cells. Out of several risk factors, glaucoma shows an increased intraocular pressure, which is not only the most important symptom, but also the only treatable symptom.

Xalatan, which uses latanoprost as an active ingredient, is a representative therapeutic agent for glaucoma, showing an effect of lowering the intraocular pressure, and it is a first drug based on a prostaglandin analogue (PGA), approved by the Food and Drug Administration (FDA) in 1996. Out of prostaglandin-based products, the Xalatan comprises the highest concentration of benzalkonium chloride (BAK, 0.02% w/v), wherein benzalkonium chloride is used for the purpose of not only obtaining preservative effect, but also solubilizing and stabilizing latanoprost.

However, it is reported that preservatives such as benzalkonium chloride show toxicity to corneal epithelial cells and delay the regeneration of epithelial cells (J Korean Ophthalmol Soc 2010; 51(8):1113-1120). Thus, in order to avoid a side effect by usage of eye drops, it is preferable to reduce a concentration of preservatives such as benzalkonium chloride as much as possible. Because the administration of glaucoma medicine is required for a long time, it is necessary to develop a therapeutic agent for lowering an intraocular pressure, without comprising preservatives such as benzalkonium chloride.

Also, the Xalatan should be protected from light and stored under refrigeration at 2° to 8° C. because the Xalatan is unstable at room temperature in spite of using benzalkonium chloride. Thus, the storage condition of the Xalatan is less convenient for patients with glaucoma, who need a medication for a long time. Accordingly, it is necessary to develop a stable latanoprost ophthalmic solution, which is enough to be stored at room temperature.

A preparation using latanoprost as an active ingredient has a disadvantage, in that such preparation has a decrease in storage stability at room temperature, and thus may have an increase in occurrence of related substances such as impurities, degradation products, etc. Also, if the related substances occur, an amount of active ingredient permeation may be decreased as much as the related substances. Thus, effort is needed to develop a latanoprost eye-drop composition, which is stable and produces a less amount of related substances.

Also, there is one of the latanoprost eye drops, which may be stored at room temperature, comprising a high amount (5%) of non-ionic surfactant (polyoxyl 40 hydrogenated castor oil, HCO-40). However, it is also known that this commercial product causes cytotoxicity to eyeballs (J Biochem Pharmacol Res. 2014 Dec. 1; 2(4): 175-184).

On the other hand, latanoprost, one of prostaglandin derivatives, is a prodrug of latanoprost acid, a medicinally effective form in the body. Latanoprost is more permeable into eye and less burning sensation than latanoprost acid, which is thus administered in a form of the prodrug, i.e., latanoprost. While latanoprost permeates into a cornea (eye), it is transformed into latanoprost acid to achieve lowering effect of an intraocular pressure. However, if latanoprost is transformed into latanoprost acid before permeating into the cornea (in the formulation), an amount of drug permeation is decreased and thus the medicinal efficacy may be reduced and side effects such as the burning sensation, etc. may come out. Thus, it is necessary to develop a stable formulation which may reduce an amount of latanoprost acid (European Journal of Pharmaceutics and Biopharmaceutics 2015; 95: 203-214).

Accordingly, the present inventors strived to achieve developing the stable latanoprost eye drop, which may be stored at room temperature, and identified that the latanoprost eye drop comprising sorbitol has an improvement in stability for long time, even without comprising benzalkonium chloride, that is, no matter whether to comprise benzalkonium chloride or not, thereby completing the present invention.

PRIOR ART REFERENCES

Non-Patent Document

J Korean Ophthalmol Soc 2010; 51(8):1113-1120
J Biochem Pharmacol Res. 2014 Dec. 1; 2(4): 175-184
European Journal of Pharmaceutics and Biopharmaceutics 2015; 95: 203-214

SUMMARY

Technical Problem

One objective of the present invention is to provide an ophthalmic composition comprising latanoprost, polyoxyl 40 hydrogenated castor oil and sorbitol.

Other objective of the present invention is to provide the ophthalmic composition comprising latanoprost, polyoxyl 40 hydrogenated castor oil and sorbitol, wherein an amount of the sorbitol is 4.0 to 6.0 w/v % of the total composition.

Another objective of the present invention is to provide the ophthalmic composition for lowering an intraocular pressure, comprising latanoprost, polyoxyl 40 hydrogenated castor oil and sorbitol, wherein the amount of the sorbitol is 4.0 to 6.0 w/v % of the total composition.

Yet another objective of the present invention is to provide a method for lowering the intraocular pressure, comprising a step of administering the ophthalmic composition for lowering the intraocular pressure, comprising latanoprost, polyoxyl 40 hydrogenated castor oil and sorbitol, into an individual.

Still yet another objective of the present invention is to provide a method for preventing or treating an increased intraocular pressure, ocular hypertension and glaucoma, wherein the method comprises the step of administering the ophthalmic composition comprising latanoprost, polyoxyl 40 hydrogenated castor oil and sorbitol into the individual.

Further still yet another objective of the present invention is to provide a method for preparing the ophthalmic composition for enhancing stability of latanoprost, wherein the method comprises a step of mixing latanoprost, polyoxyl 40 hydrogenated castor oil and sorbitol.

Technical Solution

In one aspect for solving the objectives above, the present invention provides an ophthalmic composition comprising latanoprost, polyoxyl 40 hydrogenated castor oil and sorbitol, wherein an amount of the sorbitol is 4.0 to 6.0 w/v % of the total composition.

The ophthalmic composition according to the present invention is prepared by appropriately mixing the components, and has advantages of: having excellent transmission and storage stability compared to other commercial eye drops in the market; maintaining an effect of lowering an intraocular pressure; and producing a less amount of related substances.

In the present invention, the "latanoprost" is a kind of prostaglandin analogues, which may be effective for lowering the intraocular pressure, such as lowering a hyper intraocular pressure or preventing an increase of the intraocular pressure. The prostaglandin analogues include bimatoprost, tafluprost, travoprost, unoprost and the like as well as latanoprost.

The latanoprost may be comprised in a therapeutically effective amount, in order to achieve the objective of lowering the intraocular pressure. For the objectives of the present invention, an amount of latanoprost may be 0.001 to 0.05 w/v %, particularly 0.002 to 0.01 w/v %, and more particularly 0.005 w/v % based on the total amount of the ophthalmic composition, but not limited thereto.

The ophthalmic composition of the present invention shows the effect of lowering the intraocular pressure due to its nature of comprising latanoprost, and thus such composition may be valuably used in preventing or treating the increased intraocular pressure, ocular hypertension, glaucoma or any symptoms related thereto.

In preparing an ophthalmic preparation, a composition using benzalkonium chloride for stabilization of latanoprost has been disclosed, but it is also known that a use of benzalkonium chloride may cause a side effect of showing toxicity to corneal epithelial cells. Also, a composition, which may be stored at room temperature by adjusting a pH of the preparation, has been disclosed, but an administration of the preparation with a low pH may become a cause of a sensory eye irritation. Thus, in order to solve the above-mentioned problems, the present invention has prepared the ophthalmic composition, which has a pH similar to a tear film, has excellent stability, and reduces a side effect by comprising polyoxyl 40 hydrogenated castor oil and sorbitol as constituent components of the ophthalmic preparation, even without using benzalkonium chloride, that is, no matter whether to comprise benzalkonium chloride or not.

In the present invention, the "polyoxyl 40 hydrogenated castor oil" is one kind of solubilizers, and is also called PEG-40 hydrogenated castor oil as a name of the International Nomenclature Cosmetic Ingredient (INCI), in which cosmetic ingredients are internationally given names by the Personal Care Products Council (PCPC), the former Cosmetic, Toiletry and Fragrance Association (CTFA).

In the present invention, the polyoxyl 40 hydrogenated castor oil may be used in combination with HCO-40 or Cremophor RH40 in an equal sense. The polyoxyl 40 hydrogenated castor oil may show the same effect as surfactant, which is used to solubilize a water-insoluble substance.

An amount of the polyoxyl 40 hydrogenated castor oil may be 0.3 to 2.0 w/v %, particularly 0.3 to 1.0 w/v %, more particularly 0.4 to 0.7 w/v %, and much more particularly 0.5 to 0.6 w/v % of the total ophthalmic composition of the present invention.

At too high a concentration, a non-ionic surfactant such as the said polyoxyl 40 hydrogenated castor oil may lead to a side effect by causing irritation to a corneal epithelial layer. Thus, it is preferable to comprise a low amount of the non-ionic surfactant.

In one Experimental Example of the present invention, the ophthalmic composition, which was prepared by varying an amount of polyoxyl 40 hydrogenated castor oil, was kept under a stress condition (55° C. and a relative humidity of 75%) for four weeks, and then transmission thereof was measured. As a result, if an amount of polyoxyl 40 hydrogenated castor oil is less than or equal to about 1.0 w/v % of the total composition, it might be seen that an initial transmission and the transmission after storage are all excellent. On the other hand, if the amount of polyoxyl 40 hydrogenated castor oil is 2.0 w/v %, it might be seen that the initial transmission is remarkably low (Table 3).

Also, in one Experimental Example of the present invention, the ophthalmic composition, which was prepared by varying the amount of polyoxyl 40 hydrogenated castor oil, was kept under the stress condition for four weeks, and then an amount of latanoprost thereof was measured. As a result, if the amount of polyoxyl 40 hydrogenated castor oil is more than or equal to 0.3 w/v % of the total composition, it might be seen that the amount of latanoprost is maintained at a certain level after storage. On the other hand, if the amount of polyoxyl 40 hydrogenated castor oil is 0.05 w/v % and 0.1 w/v % of the total composition, it might be seen that the amount of latanoprost after storage is decreased and thus stability thereof becomes remarkably low (Table 4).

In the present invention, the "sorbitol" is a sugar alcohol having six hydroxyl groups, and is also called D-sorbitol or D-glucitol.

In one Experimental Example of the present invention, after storing the composition not comprising sorbitol, it was identified that stability thereof becomes low due to a decrease in the amount of latanoprost, and thus it might be seen that sorbitol is a constituent component for enhancing stability of the ophthalmic composition (Table 4 and Example 5).

The amount of the sorbitol may be 4.0 to 6.0 w/v %, particularly 4.0 to 5.0 w/v %, more particularly 4.1 to 4.7 w/v %, preferably about 4.4 w/v %, and most preferably 4.41 w/v % of the total ophthalmic composition.

In preparing the composition of the present invention, a D-sorbitol solution may be used to comprise sorbitol in the composition. In case of using the D-sorbitol solution, an amount of input of D-sorbitol solution may be adjusted by considering the amount of sorbitol comprised in the D-sorbitol solution such that a desired amount of sorbitol may be comprised in the total composition. Particularly, the D-sorbitol solution may be the D-sorbitol solution, in which the content of sorbitol is 70% (w/w), but not limited thereto.

Particularly, if a concentration of D-sorbitol solution comprised in the total ophthalmic composition is 70% (w/w), the D-sorbitol solution 70% (w/w) may be comprised in an amount of 6.3 w/v % of the total composition.

In one Experimental Example of the present invention, the ophthalmic composition comprising sorbitol and the ophthalmic composition not comprising the same were kept under the stress condition (55° C. and RH 75%) for four weeks, and then the contents of latanoprost thereof were measured, and amounts of related substances generated therefrom were measured. As a result, it might be seen that the ophthalmic composition comprising sorbitol maintains a high content of latanoprost, thus suggesting that such composition shows excellent storage stability (Table 4 and FIG. 5). Also, it might be seen that there is a low amount of related substances generated, which have an adverse effect on stability and quality of the ophthalmic composition (Table 5 and FIG. 6).

Also, in one Example of the present invention, the ophthalmic composition, which was prepared by varying the amount of sorbitol comprised in the composition, was kept under the stress condition (55° C. and RH 75%) for four weeks, after which the amount of latanoprost thereof and related substances was measured. As a result, as the amount of sorbitol gets higher, it might be seen that the content of latanoprost gets higher (Table 4), and the content of related substances generated gets lower (Table 5 and FIG. 6).

On the other hand, the sorbitol may perform a function of an isotonic agent, and a hypertonic eye drop may cause damage to cells. Thus, considering that an osmotic pressure of a tear film is about 300 mOsmol/kg, it is preferable that the amount of the sorbitol should not exceed 6 w/v % of the total ophthalmic composition. Also, if the amount of the sorbitol is high, particularly more than 10 w/v %, and more particularly more than 7 w/v % of the total ophthalmic composition, the amount of related substances generated is increased during storage, and thus may not be suitable for preparing the ophthalmic composition.

In the present invention, the ophthalmic composition may further comprise a stabilizer. In case of further comprising the stabilizer, the ophthalmic composition of the present invention may have much improvement in the physical and chemical stability thereof. The stabilizer is hydrated in aqueous solvent to form a certain bonding structure, in which the oil droplets of eye drops are made into a gel network, such that the stabilizer may give viscosity to the eye drops and play a role in physically stabilizing the eye drops. The stabilizer may include: cellulose-based compounds including carboxymethyl cellulose (CMC), hydroxypropylmethyl cellulose (HPMC), hydroxyethyl cellulose (HEC), etc.; polyvinyl-based compounds including polyvinyl alcohol (PVA), polyvinyl pyrrolidone (PVP), etc.; acrylic-based compounds including carbomer, etc.; gum-based compounds including gellan gum, xanthan gum, etc.; polysaccharides including hyaluronic acid (HA), sodium hyaluronate, sodium alginate, dextran, etc.; any combinations thereof; or the like. Particularly, the stabilizer may be a carbomer.

In the present invention, the ophthalmic composition may further comprise a pH adjuster, isotonic agent, preservative, buffer solution or the like.

The ophthalmic composition of the present invention has a pH suitable to be administered into eyes, wherein the pH may be adjusted by means of a method known to those skilled in the art in order to obtain an appropriate pH.

The pH of the ophthalmic composition of the present invention may be particularly 5.5 or more, and more particularly 6.5 to 7.5.

As the pH adjuster, sodium hydroxide, hydrochloric acid, etc. may be used. The pH adjuster may be used, in such a way that it is added in an amount needed to obtain an appropriate pH by means of a method known to those skilled in the art.

As the isotonic agent, at least one selected from the group including glycerol, mannitol, sodium chloride, potassium chloride, boric acid, borax and the like may be used, but not limited thereto, wherein an amount thereof may be in a range of 0.01 to 10.0 w/v %, particularly 0.1 to 3.0 w/v % with regard to the amount of the total composition.

The preservative of the present invention may include: quaternary ammonium compounds including benzalkonium chloride, benzethonium chloride, cetalkonium chloride, polyquaternium-1 (e.g., Polyquad®), etc.; guanidine-based compounds including PHMB, chlorohexidine, etc.; chlorobutanol; mercury-based antiseptics including thiromesal, phenylmercuric acetate, phenylmercuric nitrate and the like; and oxidative preservatives including a stabilized oxychloro complex (e.g., Purite®), p-hydroxybenzoate alkyls (e.g., methyl p-hydroxybenzoate (PM)), etc.

The preservative may be used by considering a side effect of eye drops, wherein an amount of the preservative may be in a range of 0.001 to 0.5 w/v % of the amount of the total composition.

As a buffer of the present invention, a buffer used in eye drops may be used without limitation, wherein an acetate buffer, citrate buffer, phosphate buffer (e.g., sodium hydrogen phosphate or hydrates thereof, and sodium dihydrogen phosphate or hydrates thereof), boric acid buffer such as boric acid or salts thereof, etc. may be used, but not limited thereto. An amount of the buffer used may be appropriately selected by those skilled in the art, and may be used in an amount of 0.001 to 10 w/v %, particularly 0.01 to 5.0 w/v %, and more particularly 0.1 to 2.0 w/v % with regard to the amount of the total composition.

In the present invention, the ophthalmic composition may be characterized by not comprising a co-gelling agent/co-solubilizing agent.

The "co-gelling agent/co-solubilizing agent" is a general component used in preparing eye drops, and may be used to obtain a desired level of viscosity and strengthen solubilization of an active component. In general, the co-gelling agent/co-solubilizing agent includes polymers such as polyethylene glycol (PEG) and vinyl derivatives including polyvinyl alcohol (PVA) or polyvinyl pyrrolidone (PVP).

In one Experimental Example of the present invention, it was identified that a composition not comprising PEG4000 has excellent storage stability and a low amount of related substances generated, and thus it might be seen that it is possible to provide a composition, in which an active component thereof is solubilized, and which is stable and has an excellent effect of lowering an intraocular pressure even without comprising the co-gelling agent/co-solubilizing agent such as PEG4000.

Also, the ophthalmic composition of the present invention not only shows an effect of reducing a side effect such as a feeling of irritation caused by foreign matters, which may occur upon an administration of eye drops by not comprising the co-gelling agent/co-solubilizing agent such as PEG4000, but also shows an excellent sensation of instillation compared to a composition comprising PEG4000 at the same time.

Also, the ophthalmic composition may be characterized by not comprising benzalkonium chloride (BAK) at all or comprising only a small amount thereof as a solubilizer. To comprise only the small amount of benzalkonium chloride (BAK) means that there is no need to comprise a large amount of benzalkonium chloride, just as in Xalatan, which comprises an excessive amount of benzalkonium chloride as the solubilizer, and also means that a minimum amount of benzalkonium chloride may be comprised to obtain a preservative capacity.

It is preferable that the ophthalmic composition of the present invention should not comprise benzalkonium chloride.

If the ophthalmic composition of the present invention comprises benzalkonium chloride as a preservative, the said benzalkonium chloride may be comprised in an amount of 0.001 to 0.01 w/v % of the amount of the total composition.

The "benzalkonium chloride" is a nitrogen cationic surfactant belonging to quaternary ammonium salts, and may be generally comprised in eye-drop compositions to play a role as a preservative, but may show a side effect such as toxicity, etc., if being comprised in an amount of a certain level or more.

In one Experimental Example of the present invention, the stability of storage at room temperature was compared between a commercially available eye drop comprising benzalkonium chloride and the ophthalmic composition of the present invention not comprising benzalkonium chloride. As a result, it might be seen that the commercially available eye drop does not secure the storage stability at room temperature, in spite of comprising a considerable amount of benzalkonium chloride for solubilization and stabilization, but the ophthalmic composition of the present invention has the excellent storage stability at room temperature. Also, it might be seen that the ophthalmic composition of the present invention may reduce a side effect caused by a long-term administration of eye drops by not comprising benzalkonium chloride at all or by comprising only a minimum amount of benzalkonium chloride needed as a preservative, and may secure stability, even without comprising benzalkonium chloride (FIGS. 1 and 2).

Also, in one Experimental Example of the present invention, an amount of latanoprost acid generated was compared between the commercially available eye drop comprising benzalkonium chloride and the ophthalmic composition of the present invention after being stored under the condition of storage at room temperature, respectively. As a result, it might be seen that an amount of latanoprost acid generated from the ophthalmic composition of the present invention was decreased by at least five times compared to that of the commercially available eye drop (FIG. 3).

Thus, the ophthalmic composition of the present invention shows excellently stable at storage condition due to maintains not only a high content of latanoprost, but also a low amount of latanoprost acid, even without comprising benzalkonium chloride, that is, no matter whether to comprise benzalkonium chloride or not.

The ophthalmic composition of the present invention may further comprise an active compound. The active compound may be a drug for treating and/or preventing an ophthalmologic disease such as ocular hypertension and/or glaucoma, etc. The active compound may be a drug for increasing a release of aqueous humor; a drug for decreasing a generation of aqueous humor; and a drug for decreasing an intraocular pressure.

The active compound may be a prostaglandin-based compound or derivatives thereof; a cholinergic promotor; a beta-adrenergic antagonist (e.g., timolol); a carbonic anhydrase inhibitor (e.g., dorzolamide); or a beta-adrenergic promoter (e.g., dipivefrin), but not limited thereto, and may be a compound conventionally used in reducing the intraocular pressure in the art.

In another aspect, the present invention may provide a method for preparing the ophthalmic composition for enhancing stability of latanoprost, wherein the method comprises a step of mixing latanoprost, polyoxyl 40 hydrogenated castor oil and sorbitol.

An amount of the sorbitol may be 4.0 to 6.0 w/v %, particularly 4.0 to 5.0 w/v %, and more particularly 4.1 to 4.7 w/v % of the total ophthalmic composition of the present invention.

In the present invention, the "latanoprost," "polyoxyl 40 hydrogenated castor oil" and "sorbitol" are the same as described above.

The method for preparing the ophthalmic composition may further comprise a step of adding a pharmaceutically acceptable additive or carrier. Such pharmaceutically acceptable additive or carrier may be added in a process of preparing the ophthalmic composition without other limitation, but preferably should be added after the latanoprost is completely mixed into the composition.

Also, in another aspect, the present invention provides a method for lowering an intraocular pressure, comprising a step of administering the ophthalmic composition into an individual. The present invention provides a method for preventing or treating an increased intraocular pressure, ocular hypertension and glaucoma, comprising a step of administering the ophthalmic composition into an individual.

In the present invention, the "individual" may mean all the animals including humans, who have an increase in the intraocular pressure or are likely to do so. The animals may be not only humans but also mammals such as a cow, horse, sheep, pig, goat, camel, antelope, dog, cat, etc., which need a treatment for symptoms similar to the increase in the intraocular pressure, but not limited thereto.

In the present invention, the "administration" means to introduce the ophthalmic composition of the present invention into patients by means of an appropriate method, and an administration route of the present invention is to locally administer into eyeballs, because the composition is an ophthalmic composition. The method for lowering the intraocular pressure according to the present invention includes administering the ophthalmic composition of the present invention in a therapeutically effective amount. The composition of the present invention may be administered in a pharmaceutically effective amount. The pharmaceutically effective amount means an amount enough to treat a disease at a reasonable risk/benefit ratio applicable to medical treatment and not to cause a side effect, wherein a level of effective dose may be determined according to factors including a patient's health condition, a type of disease, severity, activity of a drug, sensitivity to the drug, an administration method, an administration time, an administration route and excretion rate, a treatment period, a drug combined or concurrently used, as well as other factors well known in a medical field. Particularly, such composition may be administered once to several times a day in a split manner at a certain time interval depending on a doctor or pharmacist's decision, and may be administered in an amount of 0.01 ml to 0.1 ml per administration, but not limited thereto.

Also, in another aspect, the present invention provides a use of the ophthalmic composition comprising latanoprost, polyoxyl 40 hydrogenated castor oil (HCO-40) and sorbitol for lowering the intraocular pressure. The present invention provides a use of the ophthalmic composition comprising latanoprost, polyoxyl 40 hydrogenated castor oil (HCO-40) and sorbitol for preventing or treating an increased intraocular pressure, ocular hypertension and glaucoma.

In the present invention, the "latanoprost," "polyoxyl 40 hydrogenated castor oil," "sorbitol" and the like are the same as described above.

Also, in another aspect, the present invention provides a use of the ophthalmic composition comprising latanoprost, polyoxyl 40 hydrogenated castor oil (HCO-40) and sorbitol in preparing a drug for lowering the intraocular pressure. The present invention provides a use of the ophthalmic composition comprising latanoprost, polyoxyl 40 hydrogenated castor oil (HCO-40) and sorbitol in preparing a drug for preventing or treating the increased intraocular pressure, ocular hypertension and glaucoma.

In the present invention, the "latanoprost," "polyoxyl 40 hydrogenated castor oil," "sorbitol" and the like are the same as described above.

Advantageous Effects

An ophthalmic composition according to the present invention may be valuably used as an eye drop for lowering an intraocular pressure, which shows an excellent effect of lowering the intraocular pressure, excellent transmission, storage stability and sensation of instillation; reduces a side effect; secures storage stability at room temperature for a long period of time; is stable even at a high temperature; and is easy to be stored.

DETAILED DESCRIPTION

Hereinafter, the configuration and effects of the present invention will be described in more detail through Examples. However, the following Examples are provided only for the purpose of illustrating the present invention, and thus the content of the present invention is not limited thereto.

EXPERIMENTAL EXAMPLE 1

Experiment on Storage Stability in a Composition of Example 1 and Xalatan

Storage stability at room temperature was compared between an eye-drop composition of Example 1 and Xalatan, i.e., an eye drop comprising latanoprost sold in the market. Main components and amounts of the composition of Example 1 above are as shown in a following table 1, and such composition was prepared as follows. In accordance with the amounts described in the following table 1, sorbitol, polyoxyl 40 hydrogenated castor oil (Cremophor RH40) and latanoprost were dissolved in water for injection. In accordance with the amounts described in the following table 1, sodium edetate hydrate (sodium EDTA) and carbomer 974P were dissolved in other water for injection and pH thereof was adjusted by means of sodium hydroxide. After that, an ophthalmic composition was prepared by mixing the two prepared solutions together.

On the other hand, when preparing the ophthalmic composition, D-sorbitol solution may be used for the sorbitol. In this case, amount of D-sorbitol solution added to the composition may be adjusted such that an amount of sorbitol therein may be the same as the amount shown in the following table 1, by considering a corresponding content of sorbitol in the D-sorbitol solution.

TABLE 1

| Component name | Amount (w/v %) | |
| --- | --- | --- |
| | Example 1 | Xalatan |
| Latanoprost | 0.005 | 0.005 |
| Cremophor RH40 | 0.5 | — |
| Carbomer 974P | 0.1 | — |
| Sorbitol | 4.41 | — |
| Sodium EDTA | 0.05 | — |
| BAK | — | 0.02 |

The storage stability was compared between the composition and the said eye drop by respectively measuring a change in a content of latanoprost under the condition of storage at room temperature (25° C. and RH 40%) according to an elapse of the storage period.

Particularly, a content of latanoprost was analyzed by means of a high-performance liquid chromatography (HPLC), wherein conditions thereof are as follows:

(1) Mobile phase composition: Composition ratio of phosphate buffer solution 50% and acetonitrile 50%

Figure 1:
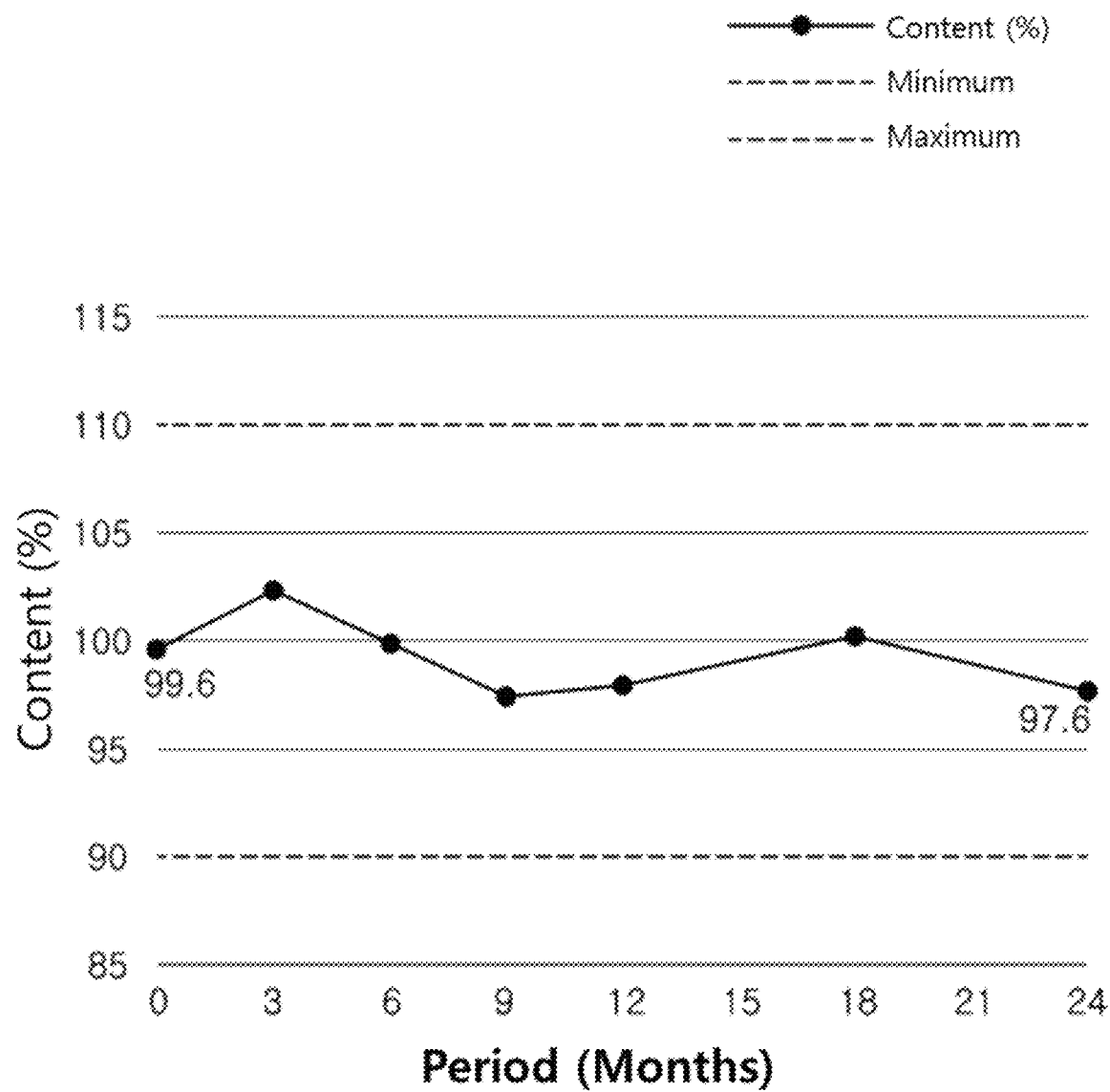
FIG. 1 is a graph of showing stability of a composition of Example 1 under the condition of storage at a room temperature (25° C. and RH 40%) for 24 months.
Figure 2:
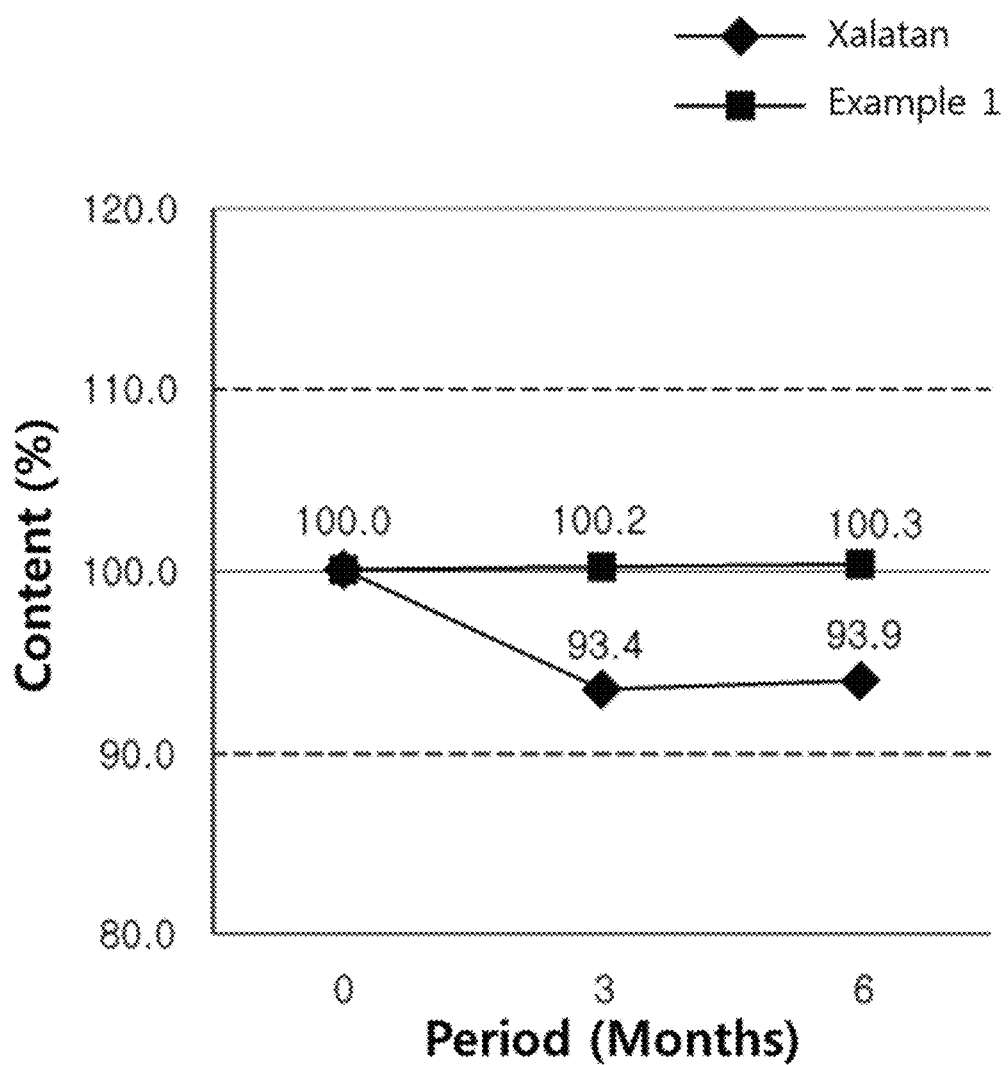
FIG. 2 is a graph of comparing the stability between the composition of Example 1 and Xalatan according to a storage period.

(2) Mobile phase velocity: 0.7 to 1.0 mL/min (3) Column: L1, particle size of 5 μm, 4.6×250 mm As a result, it was identified for the composition of Example 1 that an initial content of latanoprost is maintained even in six months after being stored under the condition of storage at room temperature, and the stability thereof is secured for at least 24 months (FIG. 1). On the other hand, it was identified for Xalatan that the content of latanoprost is decreased to 93.4% in three months after being stored, and then decreased to less than 90.0% when being stored for a long period of time, suggesting that the stability is low as a drug medicine for storage at room temperature (FIG. 2).

Thus, it was identified that the ophthalmic composition of Example 1 above has excellent storage stability compared to Xalatan sold in the market.

EXPERIMENTAL EXAMPLE 2

Experiment on Occurrence of Latanoprost Acid in the Composition of Example 1 and Xalatan An amount of latanoprost acid generated was compared between the composition of Example 1 of Experimental Example 1 above and Xalatan according to the storage period.

Particularly, the amount of latanoprost acid generated was analyzed by means of the HPLC, wherein conditions thereof are as follows:

(1) Mobile phase composition: Mobile phase gradient conditions between phosphate buffer solution and acetonitrile over time.

Figure 3:
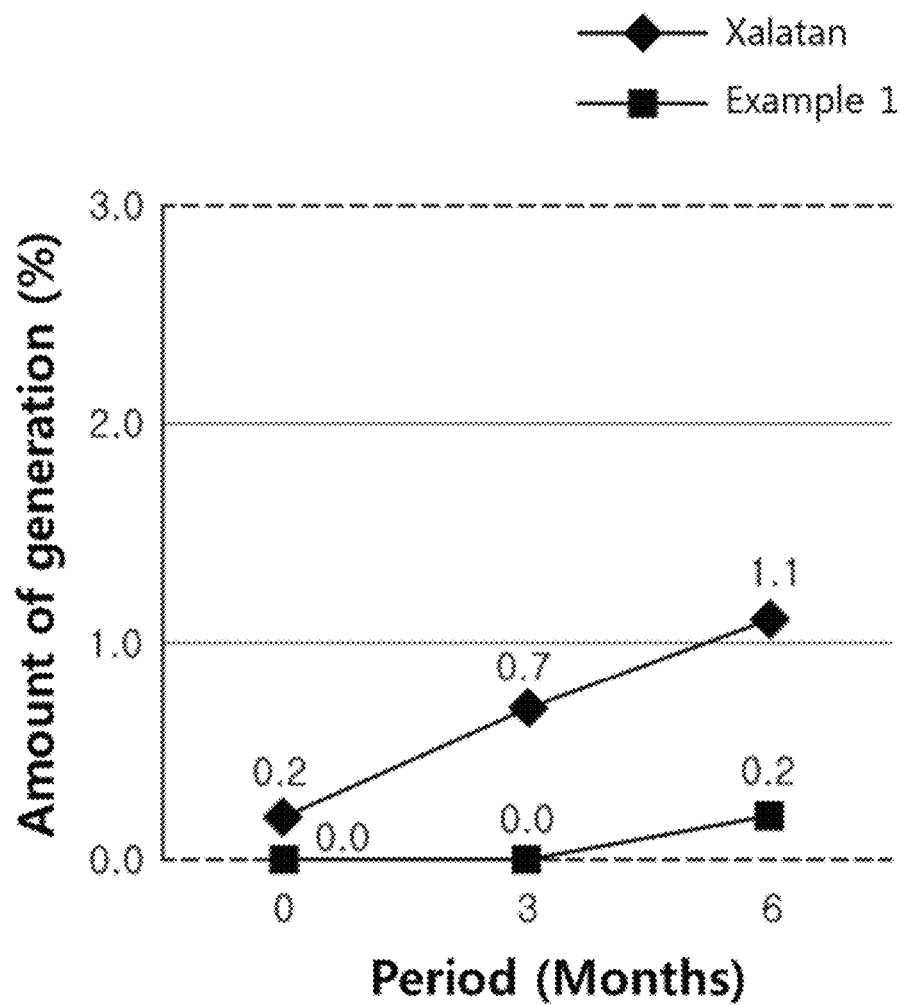
FIG. 3 is a graph of comparing an amount of latanoprost acid generated between the composition of Example 1 and Xalatan according to the storage period.

(2) Mobile phase velocity: 0.5 to 0.8 mL/min (3) Column: Chiral column, particle size of 3 μm, 4.6×250 mm As a result, it was identified for the composition of Example 1 that only 0.2% of latanoprost acid is generated even in six months after being stored under the condition of storage at room temperature. On the other hand, it was identified for Xalatan that 1.1% of latanoprost acid is generated in six months after being stored, suggesting that latanoprost acid is generated at least five times more compared to the composition of Example 1 (FIG. 3).

Thus, it was identified for the eye-drop composition of Example 1 above that the amount of latanoprost acid generated is suitable in accordance with criteria for products, and the amount of latanoprost acid generated is remarkably low compared to Xalatan.

EXPERIMENTAL EXAMPLE 3

Experiment on Transmission Under a Stress Condition

Ophthalmic compositions of Examples and Comparative Example in a following table 2 were stored under a stress condition (55° C. and RH 75%) for four weeks, and then transmission of the compositions was measured.

The eye-drop compositions of Examples 2 to 4 in the following table 2 were prepared by means of the same method as shown in Experimental Example 1, and the composition of Comparative Example 1 was prepared as follows. In accordance with the amounts described in the following table 2, PEG4000, sorbitol, polyoxyl 40 hydrogenated castor oil (Cremophor RH40) and latanoprost were dissolved in water for injection. In accordance with the amounts described in the following table 2, sodium edetate hydrate (sodium EDTA) and carbomer 974P were dissolved in other water for injection and pH thereof was adjusted by means of sodium hydroxide. After that, the composition was prepared by mixing the said two prepared solutions together.

A transmission of the compositions was measured by means of an UV spectrophotometer (Shimazu), and the transmission (T550%) was measured at 550 nm by using purified water as a blank.

TABLE 2

| | Amount (w/v %) | | | |
|---|---|---|---|---|
| Component name | Example 2 | Example 3 | Example 4 | Comparative Example 1 |
| Latanoprost | 0.005 | 0.005 | 0.005 | 0.005 |
| Cremophor RH40 (HCO-40) | 0.5 | 1.0 | 2.0 | 5.0 |
| Carbomer 974P | 0.1 | 0.1 | 0.1 | 0.1 |
| Sorbitol | 2.45 | 2.45 | 2.45 | 3.5 |
| Sodium EDTA | 0.05 | 0.05 | 0.05 | 0.05 |
| PEG4000 | — | — | — | 1 |

Figure 4:
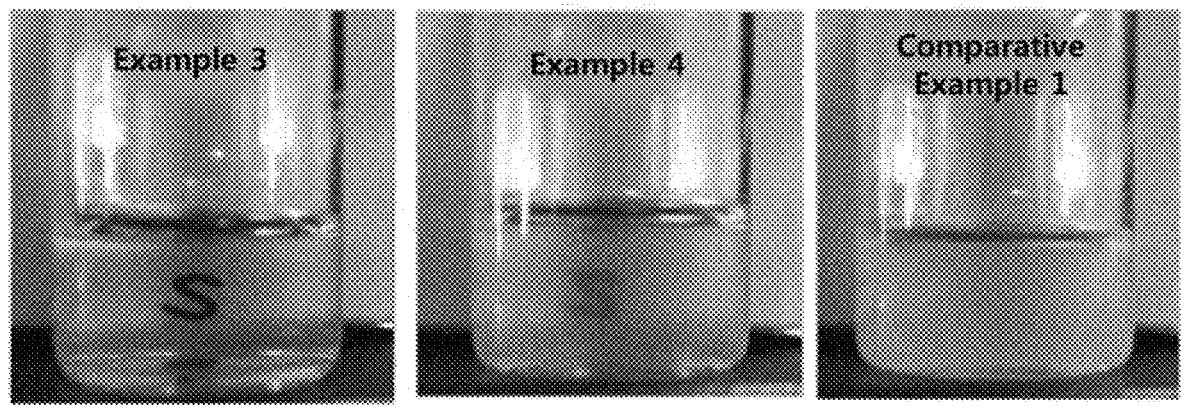
FIG. 4 is a picture of comparing transmission between compositions of Examples 3 and 4 and a composition of Comparative Example 1.

As a result of measuring the transmission of the compositions, the composition of Example 2 showed a high initial transmission of 90% or more, while the composition of Comparative Example 1 showed a very low initial transmission of 20% or less. Also, it was identified for the composition of Comparative Example 1 that the transmission is also 15% in four weeks after being stored, which is at least 75% lower compared to the composition of Example 2 (Table 3). Also, it was identified for compositions of Examples 3 and 4 that the transmission is decreased about 4% and 8% respectively after being stored for four weeks compared to an initial value, while the transmission of the composition of Example 2 is uniformly maintained at a level of 98% even under the stress condition (FIG. 4 and Table 3). Also, when comparing the initial transmission between the two compositions, it was identified that a low transmission is shown in the case of comprising a high amount of HCO-40 as shown in Example 4, and a very low transmission is shown in the case of comprising a high amount of HCO-40 and PEG4000 as shown in Comparative Example 1 (Table 3).

Thus, it might be seen that components of the ophthalmic composition and amounts thereof are constituent components having an influence on turbidity of composition properties and turbidity thereof over time.

TABLE 3

| | Transmission (%) | | | |
|---|---|---|---|---|
| | Example 2 | Example 3 | Example 4 | Comparative Example 1 |
| Initial | 98 | 95 | 69 | 18 |
| In four weeks later | 98 | 91 | 61 | 15 |

EXPERIMENTAL EXAMPLE 4

Experiment on Storage Stability Under the Stress Condition

Ophthalmic compositions of Examples in a following table 4 were prepared by means of the same method as shown in Experimental Example 1 above, then charged into LDPE eye drop containers, and then stored under the stress condition (55° C. and RH 75%) for four weeks. After that, a content of latanoprost in the compositions was measured by means of the same method as shown in Experimental Example 1 above.

Figure 5:
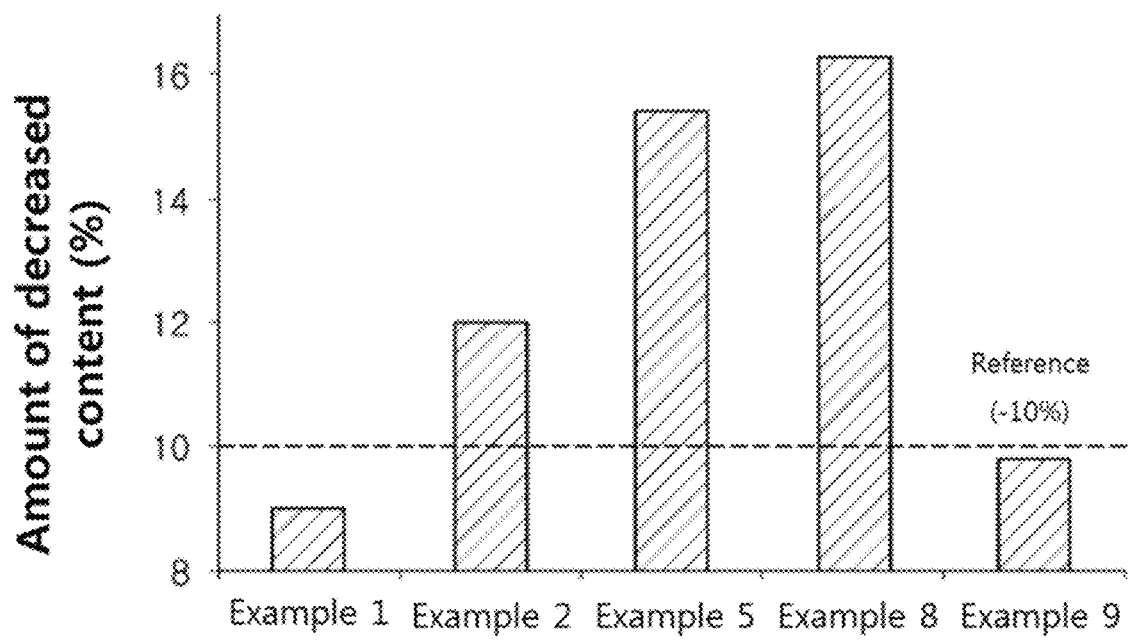
FIG. 5 is a graph of showing a decreased amount in a content of a main component (latanoprost) of compositions of Examples 1, 2, 5, 8 and 9 during storage.

As a result, it was identified for the composition of Example 5 not comprising sorbitol that a content of latanoprost becomes too low to secure stability of the ophthalmic composition after being stored for four weeks, but the higher amount of sorbitol is, the higher content of latanoprost is, thus suggesting that stability of the composition is excellent (Table 4 and FIG. 5). On the other hand, it was identified for the composition of Example 1 that the content of latanoprost is 90% or more, thus securing the most excellent stability. Furthermore, it was identified for compositions of Examples 6 to 8, in which an amount of HCO-40 is 0.1% or less, that the content of latanoprost is 59.4%, 70.2% and 83.7% respectively, thus securing less stability (Table 4).

Thus, it might be seen that sorbitol and HCO-40 are constituent components having an effect on stability of latanoprost, which is an active component of the ophthalmic composition.

TABLE 4

| Component name | Amount (w/v %) | | | | | | |
|---|---|---|---|---|---|---|---|
| | Example 1 | Example 2 | Example 5 | Example 6 | Example 7 | Example 8 | Example 9 |
| Latanoprost | 0.005 | 0.005 | 0.005 | 0.005 | 0.005 | 0.005 | 0.005 |
| Cremophor RH40 (HCO-40) | 0.5 | 0.5 | 0.5 | 0.05 | 0.1 | 0.1 | 0.3 |
| Carbomer 974P | 0.1 | 0.1 | 0.1 | 0.1 | 0.1 | 0.1 | 0.1 |
| Sorbitol | 4.41 | 2.45 | 0 | 2.45 | 2.45 | 4.41 | 4.41 |
| Sodium EDTA | 0.05 | 0.05 | 0.05 | 0.05 | 0.05 | 0.05 | 0.05 |
| Content (%) of latanoprost in four weeks later | 91.0 | 88.0 | 84.6 | 59.4 | 70.2 | 83.7 | 90.2 |

EXPERIMENTAL EXAMPLE 5

Experiment on Occurrence of Related Substances Under the Stress Condition

Compositions of Examples in a following table 5 were prepared by means of the same method as shown in Experimental Example 1 above, and an amount of related substances generated was measured after being stored under the stress condition (55° C. and RH 75%) for four weeks. The amount of the related substances generated was measured by means of a following method.

Particularly, the amount of related substances was analyzed by means of the HPLC, wherein conditions thereof are as follows:

(1) Mobile phase composition: Composition ratio of phosphate buffer solution 50% and acetonitrile 50%
(2) Mobile phase velocity: 0.3 to 0.5 mL/min
(3) Column: Chiral column, particle size of 3 µm, 4.6×250 mm

TABLE 5

| Component name | Amount (w/v %) | | | |
|---|---|---|---|---|
| | Example 1 | Example 2 | Example 5 | Example 10 |
| Latanoprost | 0.005 | 0.005 | 0.005 | 0.005 |
| Cremophor RH40 (HCO-40) | 0.5 | 0.5 | 0.5 | 0.5 |
| Carbomer 974P | 0.1 | 0.1 | 0.1 | 0.1 |
| Sorbitol | 4.41 | 2.45 | 0 | 3.5 |
| Sodium EDTA | 0.05 | 0.05 | 0.05 | 0.05 |

Figure 6:
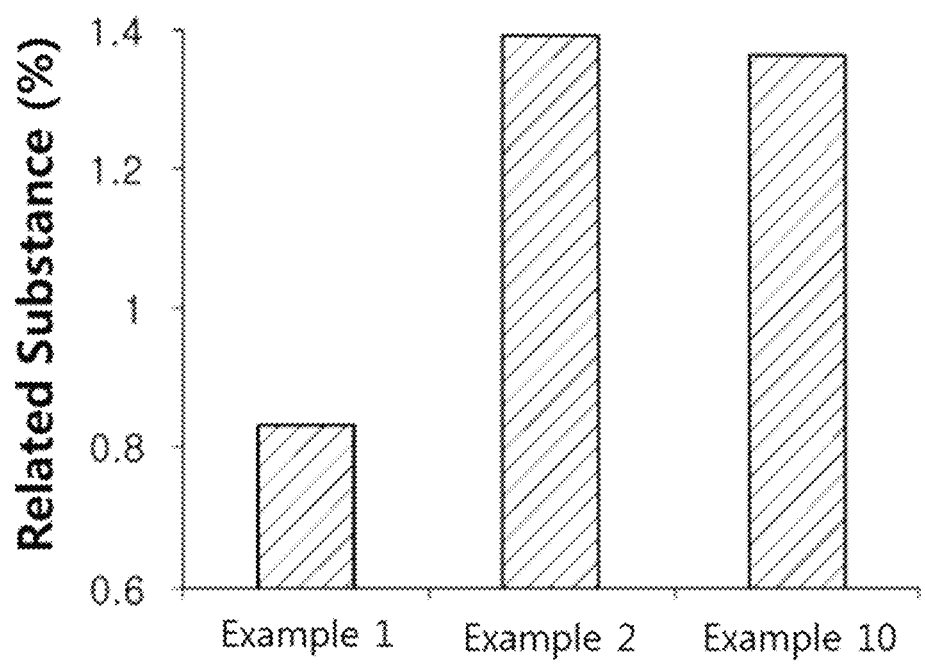
FIG. 6 is a graph of showing an amount of related substances generated from compositions of Examples 1, 2 and 10 during storage.

As a result, it was identified for the composition of Example 5 not comprising sorbitol that the amount of related substances generated is 2.86%, but it was also identified for the composition of Example 1 comprising about 4.4 w/v % of sorbitol that the amount of related substances generated is decreased to 0.83%, thus suggesting that the amount of related substances generated is about at least three times lower compared to the composition not comprising sorbitol after being stored under the stress condition, and the amount of related substances is also decreased about at least 1.6 times even compared to the composition of Example 10 (FIG. 6). It means that the amount of related substances are decreased about 40% compared to the amount of related substances generated from the composition of Example 10.

Thus, if sorbitol is comprised in the ophthalmic composition, it was identified that the amount of related substances generated is decreased. If the amount of sorbitol is at least 4.0 w/v %, particularly about 4.4 w/v % of the entire composition, it was identified that the amount of related substances generated is remarkably decreased.

EXPERIMENTAL EXAMPLE 6

Experiment on Change in Intraocular Pressure (IOP)

An effect of lowering an intraocular pressure (IOP) was compared between the eye-drop composition of the present invention and other compositions. An animal model of induced glaucoma used in Experimental Example 6 was prepared according to a known method (Eitan Z. Rath (2011), ISBN: 978-953-307-591-4, InTech).

Particularly, rabbits with induced glaucoma were divided into a positive control group (G1); a group dosed with the eye-drop composition of Example 1 prepared according to Experimental Example 1 above (G2); a Xalatan-dosed group (G3); and a Monoprost-dosed group (G4), and then dosed with each drug once a day (9 p.m.) for four weeks. The Monoprost-dosed group was dosed by using a Monoprost (Laboratoires Thea) product comprising 0.005 w/v % of latanoprost, a high amount (5%) of HCO-40 and PEG4000.

After the first administration, intraocular pressures were measured for each time zone (p.m. 9.5, 10, 10.5, 11, a.m. 0, 1, 4, 7, 9, p.m. 1 and 9) by using a tonometer. After that, the intraocular pressures were measured once every other day.

Figure 7:
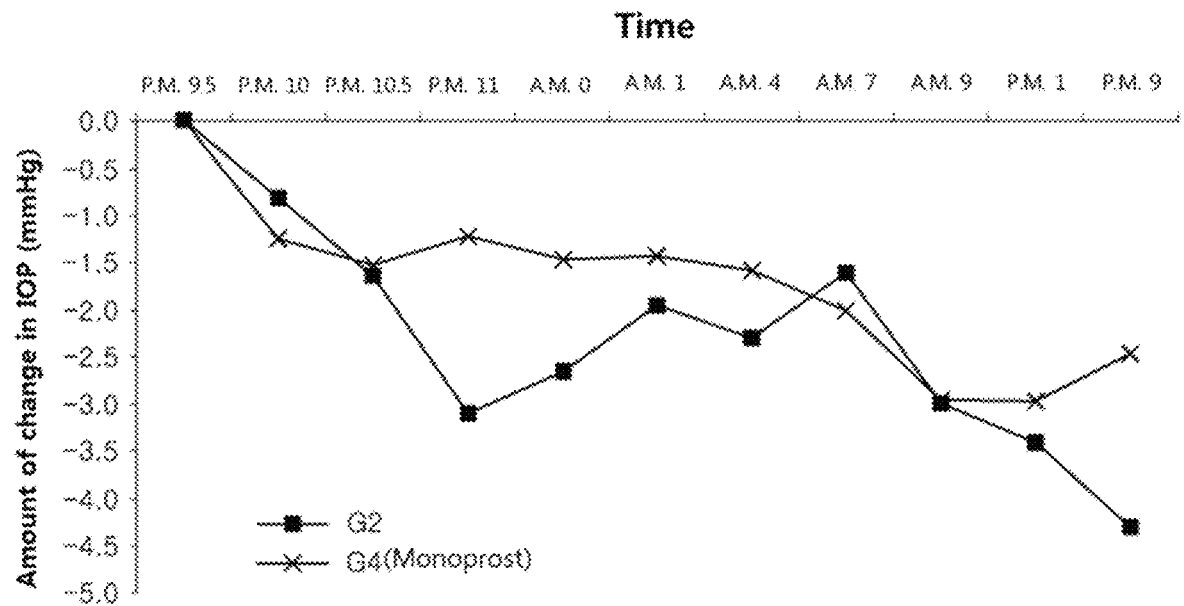
FIG. 7 is a graph of showing an amount of change in an intraocular pressure (IOP) during a day according to an administration of the composition of Example 1.

As a result of measuring the intraocular pressures for each time zone after the first administration, it was identified for the group dosed with the eye-drop composition of Example 1 (G2) that a value of intraocular pressure is lowered by about 0.5-1.5 mmHg compared to the Monoprost-dosed group (G4) from p.m. 10:30 to a.m. 5 next day, thus showing a more excellent effect of lowering the intraocular pressure (FIG. 7). From the results, it might be seen that the composition of Example 1 shows a more excellent effect of lowering the initial intraocular pressure compared to the Monoprost-dosed group (G4).

Also, considering that the intraocular pressure is increased more during sleep, it might be seen that the eye-drop composition of Example 1 shows a more effect on lowering the intraocular pressure the during nighttime zone, in which the intraocular pressure is highest, thus suggesting that composition of Example 1 shows a more excellent effect on lowering the intraocular pressure and treating glaucoma.

Figure 8:
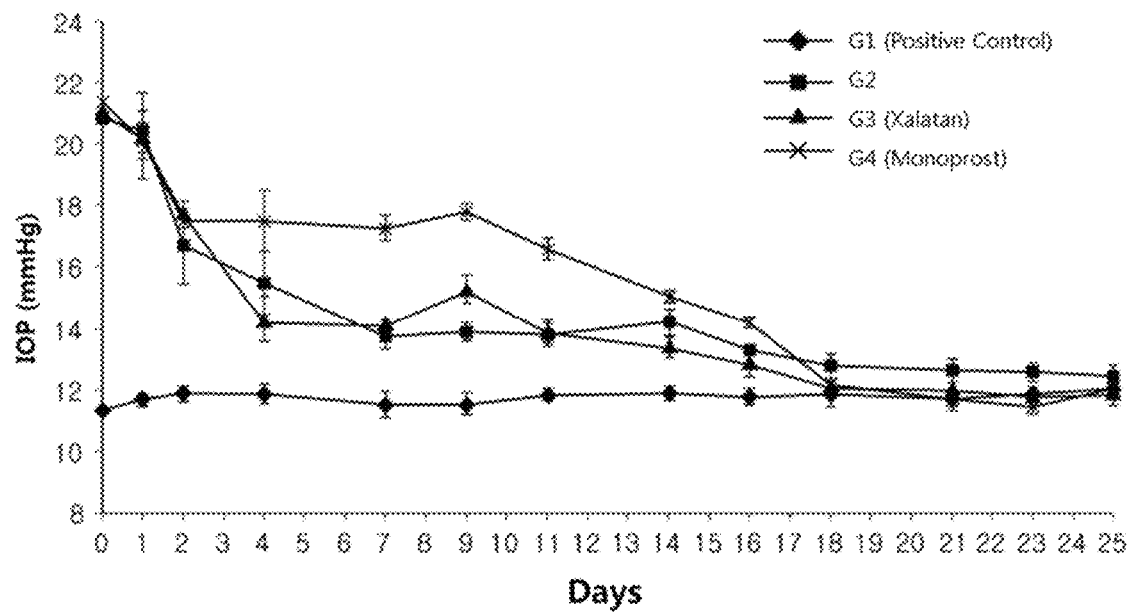
FIG. 8 is a graph of showing the IOP for 25 days according to the administration of the composition of Example 1.

As a result of measuring an amount of change in the intraocular pressure for 25 days, it was identified that the composition of the present invention may be stored at room temperature, and also shows the effect of lowering the intraocular pressure equal to Xalatan (cold storage), which have been administered as a therapeutic agent for ocular hypertension and glaucoma into many patients for a long period of time. Also, it was identified that the group dosed with the composition of the present invention (G2) shows a faster effect of lowering the intraocular pressure compared to the Monoprost-dosed group (G4) (FIG. 8). From the results, it might be seen that the composition of the present invention shows a much faster effect of lowering the intraocular pressure, thus showing an excellent effect.

From the present Experimental Example, it might be seen that the ophthalmic composition of the present invention shows a similar or excellent effect of lowering an intraocular pressure compared to other eye-drop compositions sold in the market.

While specific portions of the present invention have been described in detail above, it is apparent to those skilled in the art that such detailed descriptions are set forth to illustrate exemplary embodiments only, but are not construed to limit the scope of the present invention.

Thus, it should be understood that the substantial scope of the present invention is defined by the accompanying claims and equivalents thereto.

What is claimed is:

1. An ophthalmic composition comprising latanoprost, polyoxyl 40 hydrogenated castor oil (HCO-40) and sorbitol, wherein an amount of the HCO-40 is 0.3 to 1.0 w/v % of the total composition, and wherein an amount of the sorbitol is 4.0 to 6.0 w/v % of the total composition.

2. The ophthalmic composition according to claim 1, wherein the amount of the sorbitol is 4.1 to 4.7 w/v % of the total composition.

3. The ophthalmic composition according to claim 1, characterized in that the composition does not comprise a co-gelling agent/co-solubilizing agent.

4. The ophthalmic composition according to claim 1, wherein the amount of the polyoxyl 40 hydrogenated castor oil is 0.5 w/v % of the total composition.

5. The ophthalmic composition according to claim 1, wherein the amount of the latanoprost is 0.001 to 0.05 w/v % of the total composition.

6. The ophthalmic composition according to claim 1, wherein the composition may further comprise an active compound.

7. The ophthalmic composition according to claim 1, wherein the composition is a composition for lowering an intraocular pressure.

8. The ophthalmic composition according to claim 7, wherein the composition is used for lowering an intraocular pressure, such that the composition is used in preventing or treating an increased intraocular pressure, ocular hypertension, glaucoma or ophthalmologic diseases related thereto.

9. The ophthalmic composition according to claim 1, wherein the composition is a stabilized composition for lowering an intraocular pressure.

10. A method for stabilizing latanoprost, comprising a step of mixing latanoprost, polyoxyl 40 hydrogenated castor oil (HCO-40) and sorbitol, wherein an amount of the polyoxyl 40 hydrogenated castor oil is 0.3 to 1.0 w/v % of the total composition prepared according to the step above, and wherein an amount of the sorbitol is 4.0 to 6.0 w/v % of the total composition prepared according to the step above.

11. A method for lowering an intraocular pressure, comprising a step of administering the composition of claim 1 into an individual.

12. The ophthalmic composition according to claim 9, wherein the amount of the sorbitol is 4.1 to 4.7 w/v % of the total composition.

13. The ophthalmic composition according to claim 9, wherein the amount of the polyoxyl 40 hydrogenated castor oil is 0.5 w/v % of the total composition.

14. The ophthalmic composition according to claim 9, wherein the amount of the latanoprost is 0.001 to 0.05 w/v % of the total composition.

15. The method according to claim 10, wherein the amount of the sorbitol is 4.1 to 4.7 w/v % of the total composition.

16. The method according to claim 10, wherein the amount of the latanoprost is 0.001 to 0.05 w/v % of the total composition.

17. The method according to claim 11, wherein an amount of the latanoprost of the composition is 0.001 to 0.05 w/v % of the total composition.

* * * * *